United States Patent [19]

Ume et al.

[11] 4,014,940

[45] Mar. 29, 1977

[54] PROCESS FOR PREPARING m-PHENOXYBENZYLALCOHOL AND SIDE-CHAIN HALOGENATED m-PHENOXYTOLUENE

[75] Inventors: Yoshitaka Ume, Toyonaka; Takashi Matsuo; Nobushige Itaya, both of Nishinomiya; Nobuo Ohno, Toyonaka, all of Japan

[73] Assignee: Sumitomo Chemical Company, Limited, Osaka, Japan

[22] Filed: Jan. 18, 1974

[21] Appl. No.: 434,734

[30] Foreign Application Priority Data

Jan. 19, 1973 Japan .............................. 48-9022
Jan. 25, 1973 Japan .............................. 48-10859

[52] U.S. Cl. .................... 260/612 R; 260/613 R
[51] Int. Cl.² ............................................ C07C 41/00
[58] Field of Search ........... 260/613 R, 651 R, 600, 260/612 R, 618 H

[56] References Cited

UNITED STATES PATENTS

| 1,733,268 | 10/1929 | Kyrides .......................... 260/651 R |
| 2,231,026 | 2/1941 | Quattlebaum et al. .... 260/651 R X |
| 2,765,346 | 10/1956 | Paul et al. ................. 260/618 H X |
| 3,068,296 | 12/1962 | Wilkinson et al. ......... 260/612 R X |
| 3,280,199 | 10/1966 | Schmerling ................ 260/618 H X |
| 3,859,364 | 1/1975 | Wilson ....................... 260/618 H X |

FOREIGN PATENTS OR APPLICATIONS 6,904  2/1971  Japan

OTHER PUBLICATIONS

Wagner et al., Synthetic Org. Chem., (1953) 484.

*Primary Examiner*—Bernard Helfin
*Attorney, Agent, or Firm*—Sughrue, Rothwell, Mion, Zinn & Macpeak

[57] ABSTRACT

A process for preparing m-phenoxybenzyl, m-phenoxybenzal halides or a mixture thereof comprising halogenating m-phenoxytoluene in the presence of a phosphorus halide in the high temperature region above 220° C, and a process for preparing m-phenoxybenzylalcohol comprising halogenating m-phenoxytoluene as above, reacting the resulting side-chain halogenated m-phenoxytoluene with an alkali metal salt of acetic acid and then (a) reducing and hydrolyzing the resulting m-phenoxybenzylacetate and m-phenoxybenzaldehyde, or (b) reducing the resulting m-phenoxybenzylacetate and m-phenoxybenzaldehyde, reacting the resulting product with acetic anhydride and an alkali metal salt of acetic acid and hydrolyzing the resulting m-phenoxybenzylacetate are disclosed.

9 Claims, No Drawings

PROCESS FOR PREPARING m-PHENOXYBENZYLALCOHOL AND SIDE-CHAIN HALOGENATED m-PHENOXYTOLUENE

BACKGROUND OF THE INVENTION

1. Field of the Invention

The present invention relates to processes for preparing m-phenoxybenzylalcohol and derivatives thereof useful as pesticides. More particularly, this invention relates to 1. a process for preparing m-phenoxybenzyl and/or m-phenoxybenzal halides which comprises halogenating m-phenoxytoluene in the high temperature region above 220° C in the presence of phosphorus halides, 2. a process for preparing m-phenoxybenzylalcohol which comprises reacting the crude halogenated product obtained in the process (1) above with an alkali metal salt of acetic acid to prepare m-phenoxybenzylacetate and m-phenoxybenzaldehyde, and then reducing and hydrolyzing the resulting m-phenoxybenzylacetate and m-phenoxybenzaldehyde, and 3. a process for preparing m-phenoxybenzylalcohol which comprises reducing a mixture of m-phenoxybenzylacetate and m-phenoxybenzaldehyde and then reacting the resulting product with acetic anhydride and an alkali metal salt of acetic acid to convert m-phenoxybenzaldehyde in the mixture into m-phenoxybenzylacetate and finally hydrolyzing m-phenoxybenzlacetate 2. Description of the Prior Art In recent years, much efforts have been made to meet the need for lowering the toxicity of pesticides to mammals and cattle, however satisfactory results have not yet been obtained. It is, therefore, considered as a matter of course that the natural pesticides or their homologues, particularly insecticidal compounds called "Pyrethroid" have come to attract much attention which have widely been used for controlling insanitary insects due to their high insecticidal activities and yet showing only low toxicity to mammals.

It is regretful, however, that most of the natural pesticides cannot sufficiently be made use of their advantages because of their high price, and it has promoted investigations of insecticides of low price, high insecticidal activity and low toxicity.

SUMMARY OF THE INVENTION

The inventors, as a result of the study for a long time, found one pyrethroid of the following formula (I) which can satisfy the above requirements as disclosed in Japanese Patent Publication No. 6904/1971.

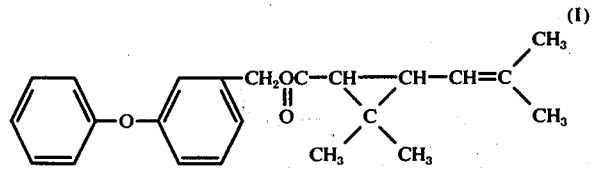

The compound of the formula (I) can be considered to be a very useful insecticide because it has a strong insecticidal activity not only to insanitary insects but also to insects harmful to agricultural and horticultural crops and stored cereals, in spite of its low toxicity to warm-blooded animals. Particularly, the activity to insanitary insects, for example houseflies, is 4 to 5 times higher than that of pyrethrin according to the test on oil sprays.

However, there has been no industrially advantageous preparation of the alcohol moiety of the compound, m-phenoxybenzylalcohol, represented by the formula (II),

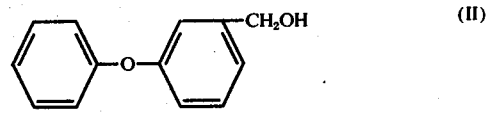

A general procedure for preparing substituted benzylalcohols is to oxidize the methyl group of m-phenoxytoluene by a suitable method and then to convert thus obtained acid into the alcohol.

For converting the methyl group linked to a benzene ring into a hydroxymethyl group, the inventors found a method according to which m-phenoxytoluene was oxidized by air to a corresponding carboxylic acid, and then the acid was esterified and reduced to obtain the alcohol in high yield. This method, however, was not economical because an expensive reducing agent such as lithium aluminum hydride was used for the reduction of carboxylic acid ester into alcohol thereby limiting the reduction of manufacturing cost in a mass production.

On the other hand, a method via halogenation of a sidechain, which is another route for converting the methyl group linked to a benzene ring into a hydroxymethyl group, is considered to be a very promising one which enables a mass production of a low-priced product.

When a radical substitution reaction is carried out for the halogenation of the aromatic side-chain, it is well known that the reaction is accompanied with side reactions competitively, that is, halogenation of the benzene ring based on an ionic reaction. The fact was also observed practically in the experiments by the present inventors that halogenation of m-phenoxytoluene, in most cases, was accompanied unavoidably with a nucleus substitution reactions, therefore producing a relatively large amount of by-products (refer to Reference Examples 1 and 2 ).

It is well known that the formation of such a nucleus-substituted product can be inhibited by the use of accelerators of the radical reaction, for example, ultraviolet rays, azobisisobutyronitrile and phosphorus trichloride. The inventors, however, could not meet with a remarkable result in the side-chain halogenation of m-phenoxytoluene in spite of the use of those catalysts (refer to Reference Example 3 ).

Furthermore, it is well known that, when the halogenation is carried out at a high temperature even if in the absence of catalysts, the resulting halogen radical reaction has the selectivity in favor of inhibiting the side reaction. The inventors' experiment, however, showed that nucleus-substituted products were produced in a relatively large amount even if the halogenation of m-phenoxytoluene was carried out in the high temperature region of 180° to 230° C (refer to Reference Example 4).

DETAILED DESCRIPTION OF THE INVENTION

The inventors, however, have extensively studied the side-chain halogenation of m-phenoxytoluene, and found an unexpected fact that only when m-phenoxytoluene of the formula (III)

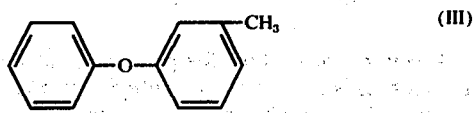
(III)

was halogenated in the high temperature region above 220° C and in the presence of phosphorus halides, the formation of nucleus-substituted products and other by-products could remarkably be inhibited, and completed the present invention after further detailed investigations.

In general, the halogen radical substitution of aromatic side-chain produces a mono-substituted product, i.e., benzylhalide a di-substituted product, i.e., benzalhalide, and a tri-substituted product, i.e., benzotrihalide, successively. The fact is clearly shown in Reference Examples and Examples of the present invention in which the reaction produces a benzylhalide of the formula (IV) with one halogen atom introduced into its side-chain,

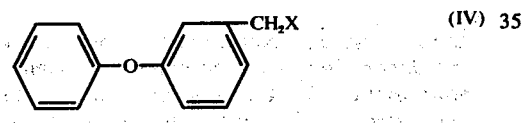
(IV)

wherein X is a chlorine or a bromine atom, and a benzalhalide of the formula (V) with two halogen atoms introduced into its side-chain,

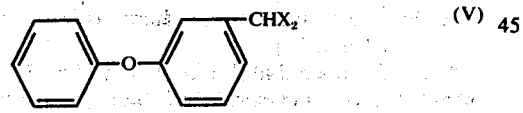
(V)

wherein X is as defined above. However, the benzalhalide is a useful product like the benzylhalide, because the benzalhalide can be converted into the desired alcohol without separating it from the benzylhalide.

The phosphorus halides which can be used for practicing the present process include phosphorus trichloride, phosphorus pentachloride and the like, and phosphorus trichloride is particularly preferred. The molar ratio of the phosphorus halide used is preferably 1/10 to 1/30 based on m-phenoxytoluene.

The reaction temperature must be set in high temperature region above 220° C in which the formation of nucleus-substituted products can remarkably be inhibited. The use of solvent is not essential for the present invention, but a high-boiling solvent such as a halogenated aromatic hydrocarbon type solvent which does not adversely affect the halogenation reaction can be used.

The reaction which leads to the formation of the desired m-phenoxybenzylalcohol (II) from a mixture of benzylhalide (IV) and benzalhalide (V) without separating them from each other will be illustrated as follows in greater detail. A mixture of two compounds is reacted with an alkali metal salt of acetic acid to obtain a mixture of m-phenoxybenzylacetate and m-phenoxybenzaldehyde of the formula (VI) and (VII), respectively.

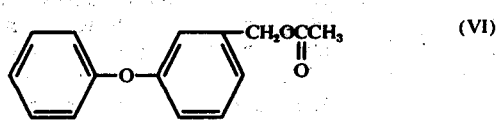
(VI)

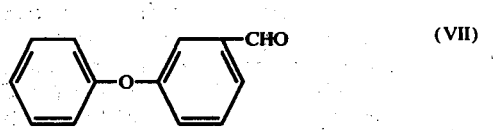
(VII)

Then, the desired m-phenoxybenzylalcohol (II) can be prepared from the mixture by 1. reducing followed by hydrolyzing the above mixture without separation,
2. reducing and hydrolyzing the mixture at the same time, or
3. first reducing the mixture, then reacting the resulting product with acetic anhydride and an alkali metal salt of acetic acid to convert m-phenoxybenzaldehyde in the mixture into m-phenoxybenzylacetate, and finally hydrolyzing the thus obtained m-phenoxybenzylacetate.

The reaction scheme of the present invention can be illustrated as follows:

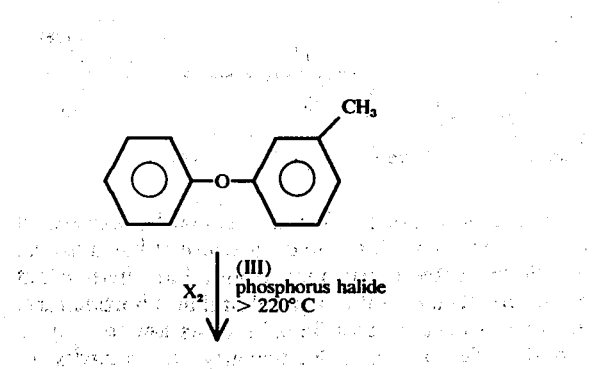

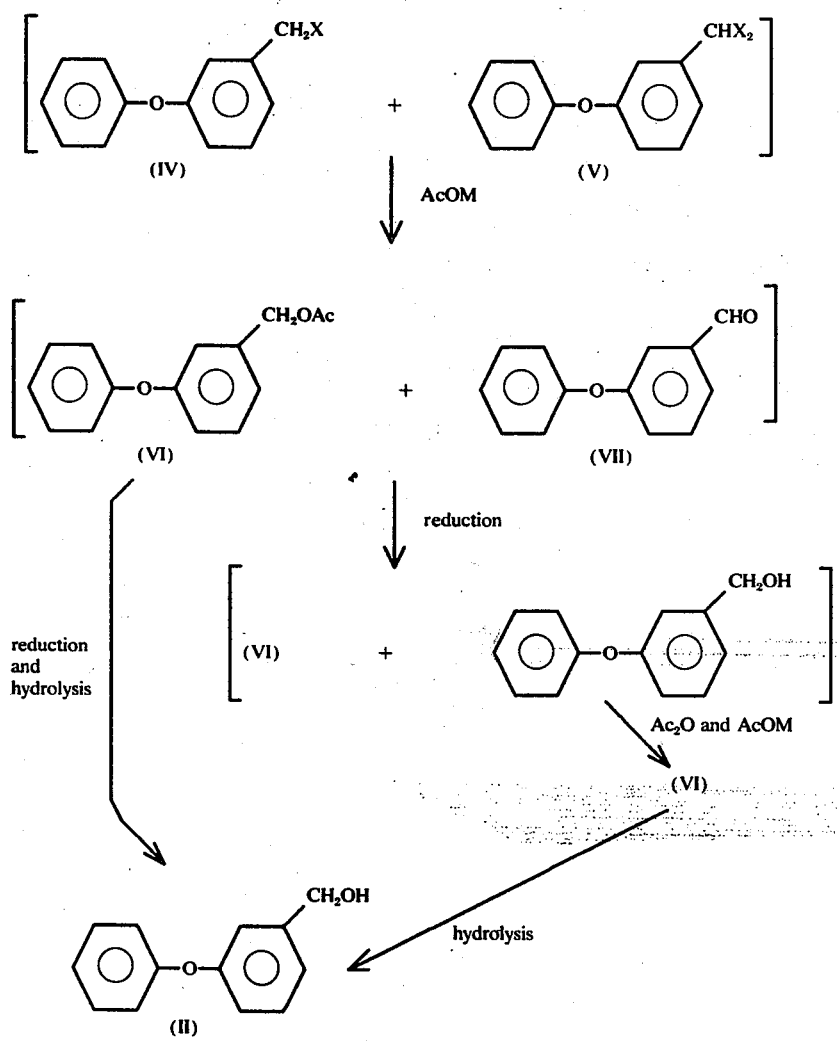

wherein M is an alkali metal.

As a result of detailed investigation of the reaction between an alkali metal salt of acetic acid and the mixture consisting of the compounds (IV) and (V), it was found that the compounds (IV) and (V) can quantitatively be converted into m-phenoxybenzylacetate (VI) and m-phenoxybenzaldehyde (VII), respectively, in the presence of a suitable solvent, for example, acetic acid, ethanol, methanol and tetrahydrofuran. Furthermore, it was surprisingly found that an expected formation of m-phenoxybenzaldiacetate and any interaction between the compounds (IV) and (V) do not occur in the above reaction.

When the mixture of the compounds (VI) and (VII) thus prepared is reduced and acetylated according to the conventional methods, the compound (VII) can be converted into (VI) quantitatively, and, therefore, the reaction mixture produced generally contains the compound (VI) as a main product, with a small amount of m-phenoxytoluene (III) and an extremely small amount of other impurities. The compound (VI) is a very useful intermediate in industry because it is highly stable against heat. The compound (VI) thus obtained can easily be purified by a fractional distillation under reduced pressure. Then, the resulting purified compound is hydrolyzed by the conventional methods to give pure m-phenoxybenzylalcohol (II) in a quantitative yield.

Alternatively, when the mixture of compounds (VI) and (VII) of the present invention is reduced and hydrolyzed according to the conventional methods, it is possible to convert (VI) and (VII) into m-phenoxybenzylalcohol (II) in a quantitative yield. The crude m-phenoxybenzylalcohol thus obtained can be purified in a quantitative yield by removing the unreacted material, that is m-phenoxytoluene (III) and other impurities by a fractional distillation under reduced pressure.

As clearly shown in the above explanation, the process of the present invention is very economical and suitable for the mass production because m-phenoxybenzylalcohol (II) can be produced by a procedure which is industrially safe and easy without separating products obtained in each reaction step.

Next, the reaction conditions under which each reaction step of the present invention is carried out will be illustrated as follows:

A. Formation of the mixture of compounds (IV) and (V)

Catalyst: Phosphorus halides such as phosphorus trichloride or phosphorus pentachloride and preferably phosphorus trichloride can be used. The molar ratio of the phosphorus halide used is preferably 1/10 to 1/30 based on m-phenoxytoluene.

Temperature: A high temperature region above 220° C.

As the reaction is completed almost instantaneously, it can be carried out in any suitable manner, for example, in a batchwise, semi-continuous or continuous manner.

B. Formation of the mixture of compounds (VI) and (VII)

An alkali metal salt of acetic acid includes preferably anhydrous or hydrated sodium acetate and potassium acetate. Examples of a suitable solvent which can be used in the present invention are organic solvents which do not adversely affect the reaction, for example, acetic acid, ethanol, methanol, acetone, tetrahydrofuran, dimethylsulfoxide and dimethylformamide, and water. The reaction temperature may range from room temperature to 200° C, but in most cases a boiling point of the solvent employed is preferably used.

C. Formation of the desired product (II)

The product can be obtained by 1. carrying out the reaction at a room temperature for several hours using an alcoholic solution of an alkali, and a reagent which is capable of reducing an aldehyde to the corresponding alcohol, for example, sodium borohydride, or crossed Cannizzaro-reaction using an alkali and formaldehyde, or a catalytic hydrogenation using metallic catalysts such as Raney nickel and palladium followed by hydrolysis, or 2. first carrying out the reduction as described above, then acetylation using acetic anhydride and sodium acetate or potassium acetate, and finally hydrolysis.

Process for preparing compounds within the present invention will now be explained in more detail with the reference examples and the examples, which are only illustrative and do not limit the scope of the present invention.

REFERENCE EXAMPLE 1

17.05 g of chlorine was passed through 36.8 g of m-phenoxytoluene over 60 minutes at 200° C while stirring. After allowing to cool, 100 ml of benzene was added to the reaction solution. The solution was washed successively with water and a saturated aqueous sodium chloride solution, and then the benzene was evaporated in vacuo. The residual solution was distilled to obtain 42.19 g of a distillate up to 135° C/0.1 mmHg which was then analyzed by gas chromatography.

The results of the analysis showed that the distillate contains 54.8% of 3-phenoxy-6-chlorotoluene, 10.2% of m-phenoxybenzylchloride, 18.1% of other impurities, and little or no m-phenoxybenzalchloride.

REFERENCE EXAMPLE 2

38.36 g of bromine was added dropwise to 36.8 g of m-phenoxytoluene over 60 minutes at 200° C while stirring. After allowing to cool, 100 ml of benzene was added thereto. The mixture was washed successively with water and a saturated aqueous sodium chloride solution, and then the benzene was evaporated in vacuo. The residual solution was distilled to obtain 49.12 g of a distillate up to 155° C/0.1 mmHg which was then analyzed by gas chromatography.

The results of the analysis showed that the distillate contains 18.2% of 3-phenoxy-6-bromotoluene, 48.6% of m-phenoxybenzylbromide, 7.2% of m-phenoxybenzalbromide and 14.2% of other impurities.

REFERENCE EXAMPLE 3

3 g of phosphorus trichloride was added to 36.8 g of m-phenoxytoluene, and then 17.05 g of chlorine was passed therethrough at 200° C over 60 minutes while stirring. After allowing to cool, 100 ml of benzene was added thereto. The mixture was washed successively with water and a saturated aqueous sodium chloride solution, and then the benzene was evaporated in vacuo. The residual solution was distilled to obtain 43.76 g of a distillate up to 135° C/0.1 mmHg which was then analyzed by gas chromatography.

The results of the analysis showed that the distillate contains 28.1% of 3-phenoxy-6-chlorotoluene, 44.3% of m-phenoxybenzylchloride, 9.5% of m-phenoxybenzalchloride and 8.3% of other impurities.

REFERENCE EXAMPLE 4

17.05 g of chlorine was passed through 36.8 g of m-phenoxytoluene at 230° C over 60 minutes while stirring. After allowing to cool, 100 ml of benzene was added thereto. The mixture was washed successively with water and a saturated aqueous sodium chloride solution, and then the benzene was evaporated in vacuo. The residual solution was distilled to obtain 40.47 g of a distillate up to 135° C/0.1 mmHg which was then analyzed by gas chromatography.

The results of the analysis showed that the distillate contains 21.6% of 3-phenoxy-6-chlorotoluene, 36.8% of m-phenoxybenzylchloride, 9.0% of m-phenoxybenzalchloride and 12.7% of other impurities.

EXAMPLE 1

Preparation of a mixture of m-phenoxybenzylchloride and m-phenoxybenzalchloride 3.0 g of phosphorus trichloride was added to 36.8 g of m-phenoxytoluene, and then 17.05 g of chlorine was passed through the resulting mixture over 60 minutes at 250° C while stirring. After allowing the mixture to cool, 100 ml of benzene was added thereto. The mixture was washed successively with water and a saturated aqueous sodium chloride solution, and then the benzene was evaporated in vacuo. The residual solution was distilled to obtain 42.06 g of a distillate up to 135° C/0.1 mmHg which was then analyzed by gas chromatography.

The results of the analysis showed that the distillate contains 3.9% of 3-phenoxy-6-chlorotoluene, 62.3% of m-phenoxybenzylchloride, 16.3% of m-phenoxybenzalchloride and 2.4% of other impurities.

EXAMPLE 2

Preparation of a mixture of m-phenoxybenzylchloride and m-phenoxybenzalchloride 1 g of phosphorus trichloride was added to 36.8 g of m-phenoxytoluene, and then 17.05 g of chlorine was passed through the resulting mixture over 60 minutes at 250° C while stirring. After allowing the mixture to cool, 100 ml of benzene was added thereto. The mixture was washed successively with water and a saturated aqueous sodium chloride solution, and then the benzene was evaporated in vacuo. The residual solution was distilled to obtain 40.41 g of a distillate up to 135° C/0.1 mmHg which was then analyzed by gas chromatography.

The results of the analysis showed that the distillate contains 3.9% of 3-phenoxy-6-chlorotoluene, 62.2% of m-phenoxybenzylchloride, 15.4% of m-phenoxybenzalchloride and 1.7% of other impurities.

EXAMPLE 3

Preparation of a mixture of m-phenoxybenzylbromide and m-phenoxybenzalbromide 3 g of phosphorus trichloride was added to 36.8 g of m-phenoxytoluene, and then 38.36 g of bromine was added dropwise thereto over 60 minutes at 250° C while stirring. After allowing the mixture to cool, 100 ml of benzene was added thereto. The mixture was washed successively with water and a saturated aqueous sodium chloride solution, and then the benzene was evaporated in vacuo. The residual solution was distilled to obtain 48.52 g of a distillate up to 155° C/0.1 mmHg which was then analyzed by gas chromatography.

The results of the analysis showed that the distillate contains 4.1% of 3-phenoxy-6-bromotoluene, 64.3% of m-phenoxybenzylbromide, 10.1% of m-phenoxybenzalbromide and 3.2% of other impurities.

EXAMPLE 4

Preparation of a mixture of m-phenoxybenzylacetate and m-phenoxybenzaldehyde

To 40 g of the chlorinated mixture obtained by the procedure as described in Example 1 were added 28.9 g of anhydrous sodium acetate and 50 g of acetic acid, and the resulting mixture was then heated at reflux for 8 hours. After completion of the reaction, 150 ml of water was added to the reaction solution to dissolve any excess of sodium acetate, and then the solution was extracted with benzene. The extract was washed successively with an aqueous sodium bicarbonate solution, water and a saturated aqueous sodium chloride solution, and the benzene was then evaporated in vacuo to give 40.46 g of a pale brown oil.

It was found that the resulting oil contains 14.5% of m-phenoxytoluene (the starting material), 3.9% of 3-phenoxy-6-chlorotoluene (a nucleus-substituted product), 63.0% of m-phenoxybenzylacetate and 16.1% of m-phenoxybenzaldehyde.

EXAMPLE 5

Preparation of m-phenoxybenzylalcohol

To 40 g of the mixture obtained by the procedure as described in Example 4 were added 60 ml of 99.5% ethanol saturated with sodium hydroxide and 140 ml of 99.5% ethanol. To the mixture was added 1.4 g of sodium borohydride while cooling, and then the mixture was stirred at room temperature. After 6 hours, a 10% aqueous acetic acid solution was added thereto to decompose any excess of sodium borohydride, and the solution was extracted with benzene. The extract was washed successively with a saturated aqueous sodium bicarbonate solution, water and a saturated aqueous sodium chloride solution, and then the benzene was evaporated in vacuo to give 34.55 g of a pale yellow, oily substance. It was found that the substance contains 14.5% of m-phenoxytoluene (the starting material), 3.7% of 3-phenoxy-6-chlorotoluene (a nucleus-substituted product) and 81.2% of the desired product, m-phenoxybenzylalcohol.

30 g of the mixture thus obtained was then subjected to a fractional distillation using a distillation tower where the theoretical plates are about 20 to obtain 24.39 g of 98.0% purity m-phenoxybenzylalcohol as a colorless oil (B.P. 137 ~ 139° C/0.35 mmHg; purity 98.0%).

Since 3.0 g of m-phenoxytoluene, the starting material, was recovered at the same time, the overall yield of m-phenoxybenzylalcohol from m-phenoxytoluene was 80.4%.

EXAMPLE 6

Preparation of m-phenoxybenzylalcohol

To 40 g of the mixture obtained by the procedure as described in Example 4 was added 200 ml of 99.5% ethanol and to this solution was added 1.4 g of sodium borohydride while cooling. After 6 hours with stirring at room temperature, a 10% aqueous acetic acid solution was added thereto to decompose any excess of sodium borohydride and the solution was extracted with benzene. The extract was washed successively with a saturated aqueous sodium bicarbonate solution, water and a saturated aqueous sodium chloride solution, and the benzene was then evaporated in vacuo to give 38.8 g of a pale yellow oil.

It was found that the resulting oil contains 14.5% of m-phenoxytoluene, 3.8% of 3-phenoxy-6-chlorotoluene, 61.0% of m-phenoxybenzylacetate and 18.5% of m-phenoxybenzylalcohol.

To the mixture obtained above were then added 5.8g of acetic anhydride, 2.2 g of anhydrous sodium acetate and 200 ml of benzene, and the resulting solution was heated at reflux for 4 hours. After allowing the reaction solution to cool, 70 ml of water was added to the reaction solution to decompose any excess of acetic anhydride, and then the benzene layer was separated and washed successively with an aqueous sodium bicarbonate solution, water and a saturated aqueous sodium chloride solution, and the benzene was evaporated in vacuo to give 40.0 g of a pale yellow oil.

It was found that the resulting oil contains 14.4% of m-phenoxytoluene, 3.8% of 3-phenoxy-6-chlorotoluene, and 79.4% of m-phenoxybenzylacetate.

30 g of the mixture obtained above was then subjected to a fractional distillation using a distillation tower where the theoretical plates are about 20 to give 24.3 g of the m-phenoxybenzylacetate as a colorless oil (B.P. 124 ~ 127° C/0.35 mmHg; purity 97.8%). In this procedure, 2.9 g of m-phenoxytoluene was recovered at the same time.

To 24.0 g of the thus obtained purified m-phenoxybenzylacetate was added 50 ml of a 20% methanolic potassium hydroxide solution, and, after 6 hours with stirring at room temperature, the methanol was evaporated in vacuo. To the resulting residue was then added 50 ml of water, and the solution was extracted with benzene. The benzene was evaporated in vacuo to give 19.9 g of the m-phenoxybenzylalcohol as a colorless oil (purity, 97.2%). The overall yield of m-phenoxybenzylalcohol from m-phenoxytoluene was found to be 79.8%.

While the invention has been described in detail and with reference to specific embodiments thereof, it will be apparent to one skilled in the art that various changes and modifications can be made therein without departing from the spirit and scope thereof.

What is claimed is:

1. A process for preparing m-phenoxybenzyl, m-phenoxybenzal halides or a mixture thereof which comprises halogenating m-phenoxytoluene with a halogen in the presence of a phosphorus halide in the high temperature region above 220° C.

2. A process for preparing m-phenoxybenzylalcohol represented by the formula,

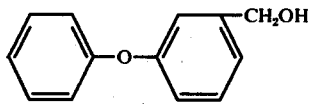

which comprises halogenating m-phenoxytoluene with a halogen in the presence of a phosphorus halide in the high temperature region above 220° C, reacting the resulting side chain-halogenated m-phenoxytoluene with an alkali metal salt of acetic acid, and then reducing and hydrolyzing the resulting m-phenoxybenzylacetate and m-phenoxybenzaldehyde.

3. The process according to claim 1, wherein said phosphorus halide is phosphorus trichloride or phosphorus pentachloride.

4. The process according to claim 1, wherein the molar ratio of phosphorus polyhalide to m-phenoxytoluene is 1/10 to 1/30.

5. The process according to claim 2, wherein the alkali metal salt of acetic acid is sodium acetate or potassium acetate.

6. The process according to claim 2, wherein said reducing is carried out in the presence of sodium borohydride at room temperature.

7. The process according to claim 2, wherein said reducing and hydrolyzing is carried out under the conditions of Cannizzaro-reaction with alkali and formaldehyde.

8. The process according to claim 2, wherein said reducing is carried out by catalytic hydrogenation in the presence of Raney nickel or palladium.

9. The process according to claim 2, wherein said reaction with an alkali metal salt of acetic acid is conducted from room temperature to 200° C.

* * * * *